United States Patent
Campin et al.

(10) Patent No.: US 12,336,759 B2
(45) Date of Patent: Jun. 24, 2025

(54) SELECTION OF INTRAOCULAR LENS BASED ON A PREDICTED SUBJECTIVE OUTCOME SCORE

(71) Applicant: Alcon Inc., Fribourg (CH)

(72) Inventors: John Alfred Campin, Southlake, TX (US); Brant Gillen, Southlake, TX (US); Martin Gründig, Rangsdorf (DE); Robert Moore, Tannay (CH); George Hunter Pettit, Fort Worth, TX (US); Mark Andrew Zielke, Lake Forest, CA (US)

(73) Assignee: ALCON INC., Fribourg (CH)

( * ) Notice: Subject to any disclaimer, the term of this patent is extended or adjusted under 35 U.S.C. 154(b) by 789 days.

(21) Appl. No.: 17/330,327

(22) Filed: May 25, 2021

(65) Prior Publication Data

US 2021/0369106 A1    Dec. 2, 2021

Related U.S. Application Data

(60) Provisional application No. 63/032,195, filed on May 29, 2020.

(51) Int. Cl.
    *A61B 3/10*      (2006.01)
    *A61B 3/00*      (2006.01)
    (Continued)

(52) U.S. Cl.
    CPC .............. *A61B 3/10* (2013.01); *A61B 3/0025* (2013.01); *A61B 3/103* (2013.01); *G06N 3/08* (2013.01);
    (Continued)

(58) Field of Classification Search
    CPC ......... A61B 3/103; A61B 3/0025; A61B 3/10; A61B 2034/108; G06N 3/08; G16H 10/20; G16H 10/60; G16H 50/30; G16H 50/20
    (Continued)

(56) References Cited

U.S. PATENT DOCUMENTS

2009/0281552 A1  11/2009  Hiramatsu et al.
2015/0316788 A1  11/2015  Holden et al.
(Continued)

FOREIGN PATENT DOCUMENTS

EP    3491996 A1    6/2019
JP    2009034451 A  2/2009
(Continued)

*Primary Examiner* — Mahidere S Sahle

(57) ABSTRACT

A system and method for selecting an intraocular lens, for implantation into an eye, includes a controller having a processor and a tangible, non-transitory memory on which instructions are recorded. The controller is configured to selectively execute a machine learning model trained with a training dataset. Execution of the instructions by the processor causes the controller to obtain pre-operative objective data for the patient, including one or more anatomic eye measurements. The controller is configured to obtain pre-operative questionnaire data for the patient, including at least one personality trait. The pre-operative objective data and the pre-operative questionnaire data are entered as respective inputs to the machine learning model. A predicted subjective outcome score for the patient is generated as an output of the machine learning model. The intraocular lens is selected based in part on the predicted subjective outcome score.

16 Claims, 2 Drawing Sheets

(51) Int. Cl.
*A61B 3/103* (2006.01)
*G06N 3/08* (2023.01)
*G16H 10/20* (2018.01)
*G16H 10/60* (2018.01)
*A61B 34/10* (2016.01)
*G16H 50/20* (2018.01)
*G16H 50/30* (2018.01)

(52) U.S. Cl.
CPC ............ *G16H 10/20* (2018.01); *G16H 10/60* (2018.01); *A61B 2034/108* (2016.02); *G16H 50/20* (2018.01); *G16H 50/30* (2018.01)

(58) Field of Classification Search
USPC .................................................. 351/205, 206
See application file for complete search history.

(56) References Cited

U.S. PATENT DOCUMENTS

| | | |
|---|---|---|
| 2019/0209242 A1 | 7/2019 | Padrick |
| 2020/0015894 A1 | 1/2020 | Bor et al. |
| 2020/0315783 A1* | 10/2020 | Rosen .............. B29D 11/00461 |

FOREIGN PATENT DOCUMENTS

| | | | | |
|---|---|---|---|---|
| JP | 2016505885 A | 2/2016 | | |
| WO | WO-2009064911 A2 * | 5/2009 | ................ | A61B 3/10 |
| WO | 2020012434 A2 | 1/2020 | | |
| WO | WO-2020047224 A1 * | 3/2020 | ........... | A61B 5/0042 |

\* cited by examiner

SELECTION OF INTRAOCULAR LENS BASED ON A PREDICTED SUBJECTIVE OUTCOME SCORE

INTRODUCTION

The disclosure relates generally to a system and method of selecting an intraocular lens for implantation in an eye. The human lens is generally transparent such that light may travel through it with ease. However, many factors may cause areas in the lens to become cloudy and dense, and thus negatively impact vision quality. The situation may be remedied via a cataract procedure, whereby an artificial lens is selected for implantation into a patient's eye. Indeed, cataract surgery is commonly performed all around the world. With different types of intraocular lenses available today, it is not always clear what the best choice for a specific patient may be.

SUMMARY

Disclosed herein is a system and method for selecting an intraocular lens for implantation into an eye of a patient. The system includes a controller having a processor and a tangible, non-transitory memory on which instructions are recorded. The controller is configured to selectively execute at least one machine learning model ("at least one" omitted henceforth). The machine learning model is trained with a training dataset.

Execution of the instructions by the processor causes the controller to obtain pre-operative objective data for the patient, including one or more anatomic eye measurements. The controller is configured to obtain pre-operative questionnaire data for the patient, including at least one personality trait. The pre-operative objective data and the pre-operative questionnaire data are entered as respective inputs to the machine learning model. A predicted subjective outcome score for the patient is generated as an output of the machine learning model. The intraocular lens is selected based in part on the predicted subjective outcome score.

The machine learning model may include a neural network. The personality trait of the patient may be represented as at least one of a numerical scale of agreeability or as a binary result, the binary result being either predominantly agreeable or predominantly non-agreeable. The pre-operative questionnaire data may further include a lifestyle needs assessment for the patient.

An integrated diagnostic device may be configured to obtain the pre-operative objective data. The pre-operative objective data further includes refractive eye measurements and physiologic eye measurements. The training dataset includes respective historical sets composed of respective pre-operative objective data, respective pre-operative personality data, respective intra-operative data, respective post-operative objective data, and respective subjective outcome data. The system may include a data management module configured to collect the respective historical sets from a plurality of electronic medical record units and deliver the respective historical sets to the at least one machine learning module. The respective subjective outcome data in the respective historical sets may include a numerical satisfaction scale.

The controller may be configured to quantify a correlation of the respective pre-operative objective data to the respective subjective outcome score in the respective historical sets and identify the respective post-operative objective data most strongly correlating with the respective subjective outcome score. The controller may be configured to identify and screen out the respective historical sets having at least one variable in the respective post-operative objective data matching with a predefined confounding parameter.

The above features and advantages and other features and advantages of the present disclosure are readily apparent from the following detailed description of the best modes for carrying out the disclosure when taken in connection with the accompanying drawings.

DETAILED DESCRIPTION

Figure 1:
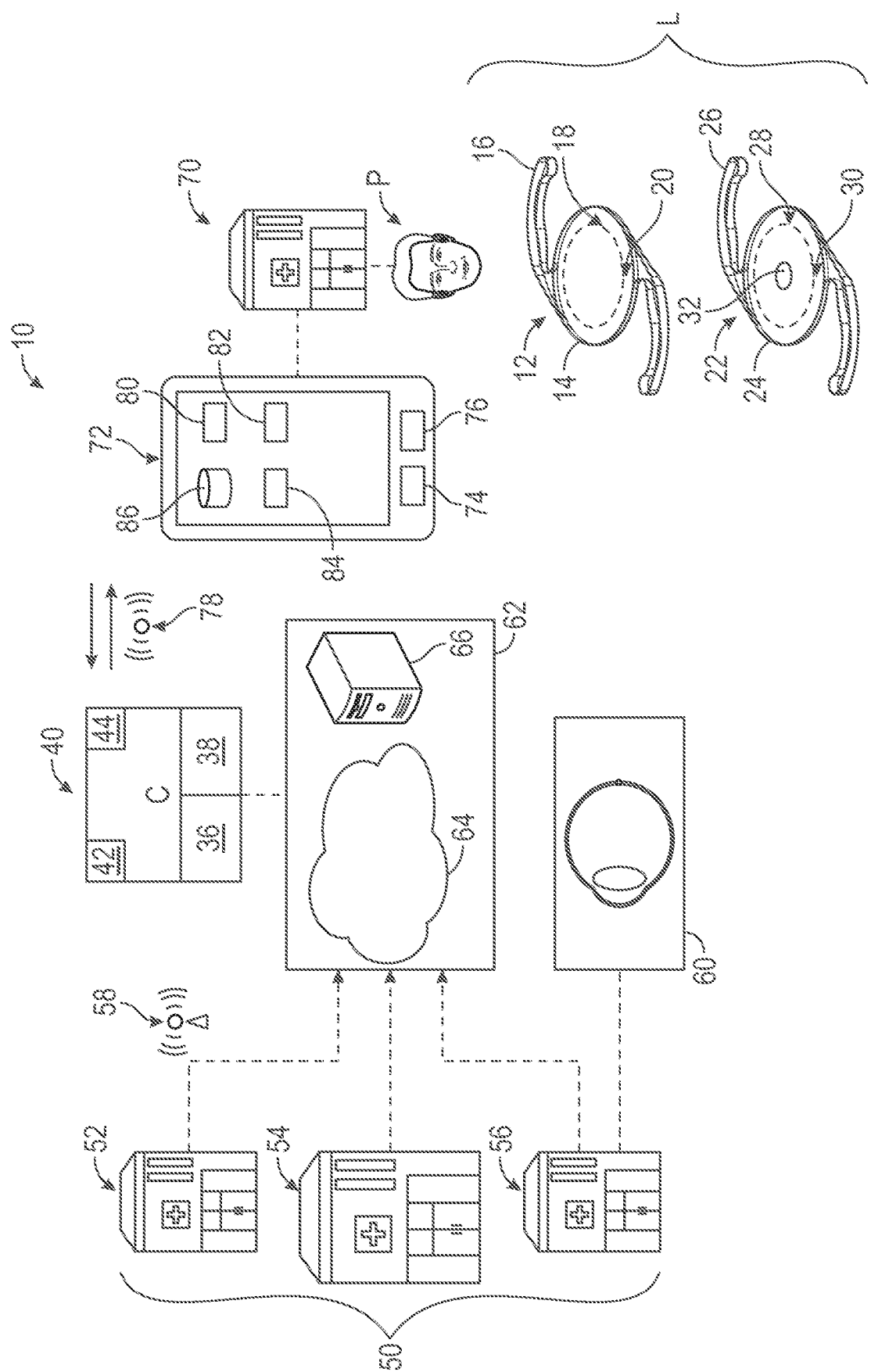
FIG. 1 is a schematic illustration of a system for selecting an intraocular lens for implantation into an eye, the system having a controller.

Referring to the drawings, wherein like reference numbers refer to like components, FIG. 1 schematically illustrates a system 10 for selecting an intraocular lens L for implantation in a patient P. As described below, the system 10 leverages both objective and subjective data for optimizing the selection process. Examples of a first intraocular lens 12 and a second intraocular lens 22 are shown in FIG. 1. While the first intraocular lens 12 and the second intraocular lens 22 are multifocal lenses in the example shown, it is understood that any type of intraocular lens L available to those skilled in the art may be employed.

Referring to FIG. 1, the first intraocular lens 12 includes an optic zone 14 contiguous with one or more supporting structures 16. The optic zone 14 may include an apodised diffractive multifocal zone 18 and an outer distance zone 20, with the first intraocular lens 12 being configured to provide good vision over a broad range of distances. Referring to FIG. 1, the second intraocular lens 22 includes an optic zone 24 contiguous with one or more supporting structures 26. The optic zone 24 may include an apodised diffractive multifocal zone 28, an outer distance zone 30 and a center distance zone 32. The second intraocular lens 22 may be configured to provide crisper distance vision and improved intermediate vision, compared to the first intraocular lens 12.

Alternatively, the intraocular lens L may be a mono-focal lens. The intraocular lens L may be an accommodating lens with a fluid-filled internal cavity, the fluid being movable in order to vary a thickness (and power) of the intraocular lens L. It is to be understood that the intraocular lens L may take many different forms and include multiple and/or alternate components.

Referring to FIG. 1, the system 10 includes a controller C having at least one processor 36 and at least one memory 38 (or non-transitory, tangible computer readable storage medium) on which instructions are recorded for executing a method 100 for selecting an intraocular lens L for the patient P. Method 100 is shown in and described below with reference to FIG. 2.

Referring to FIG. 1, the controller C is specifically programmed to selectively execute one or more machine learning models 40, such as first machine learning model 42 and second machine learning model 44. The machine learning models 40 may be embedded in the controller C. The machine learning models 40 may be stored elsewhere and accessible to the controller C. The machine learning models 40 may be configured to find parameters, weights or a structure that minimizes a respective cost function.

Referring to FIG. 1, the machine learning models 40 are trained with one or more training datasets from a plurality of facilities 50, such as first facility 52, second facility 54 and third facility 56, which may be clinical sites located all over the world. The controller C may be in communication with the plurality of facilities 50 via a first network 58. The training dataset includes respective historical sets for a large number of patients. As described below, the respective historical set includes respective pre-operative objective data, respective pre-operative personality data, respective intra-operative data, respective post-operative objective data, and respective subjective outcome data for each patient. The training datasets may be stratified based on demographic data, patients with similar-sized dimensions of eyes or other health status factors. Each of the plurality of facilities 50 may include an integrated diagnostic device 60 configured to obtain the pre-operative objective data.

Referring to FIG. 1, the system 10 may include a data management module 62 having a computerized data management system able to store information from the respective electronic medical records of the plurality of facilities 50. The data management module 62 is configured to collect the respective historical sets from the plurality of facilities 50 and provide them to the controller C. The data management module 62 may include a cloud unit 64 and/or a remote server 66 and be configured to share data across all clinical sites employing the system 10. The cloud unit 64 may include one or more servers hosted on the Internet to store, manage, and process data. The remote server 66 may be a private or public source of information maintained by an organization, such as for example, a research institute, a company, a university and/or a hospital.

Referring to FIG. 1, the patient P may be associated with a clinic 70. The controller C may be configured to receive and transmit communication with the clinic 70 through a user interface 72. The user interface 72 may be installed on a smartphone, laptop, tablet, desktop or other electronic device that a care provider at the clinic 70 may operate, for example with a touch screen interface or I/O device such as a keyboard or mouse. The user interface 72 may be a mobile application. The circuitry and components of a mobile application ("apps") available to those skilled in the art may be employed. The user interface 72 may include an integrated processor 74 and integrated memory 76. The user interface 72 may in communication with the controller C via second network 78 such that it has access to the data in the controller C.

Referring to FIG. 1, the user interface 72 may include a plurality of modules, such as a first module 80, second module 82 and third module 84. In one example, the first module 80 and the second module 82 is configured to feed input factors (pre-operative objective data and pre-operative questionnaire data, respectively) into a common or different machine learning models 40. In another example, the third module 84 is configured to obtain the output (predicted subjective outcome score) of the machine learning model 40. The user interface 72 may include a database 86 for storing and comparing the outputs (predicted subjective outcome score) of different types of intraocular lenses L.

Referring to FIG. 1, the first network 58 and/or second network 78 may be a Wireless Local Area Network (LAN) which links multiple devices using a wireless distribution method, a Wireless Metropolitan Area Networks (MAN) which connects several wireless LANs or a Wireless Wide Area Network (WAN) which covers large areas such as neighboring towns and cities. Other types of connections may be employed. The first network 58 and/or second network 78 may be a bus implemented in various ways, such as for example, a serial communication bus in the form of a local area network. The local area network may include, but is not limited to, a Controller Area Network (CAN), a Controller Area Network with Flexible Data Rate (CAN-FD), Ethernet, blue tooth, WIFI and other forms of data connection.

Figure 2:
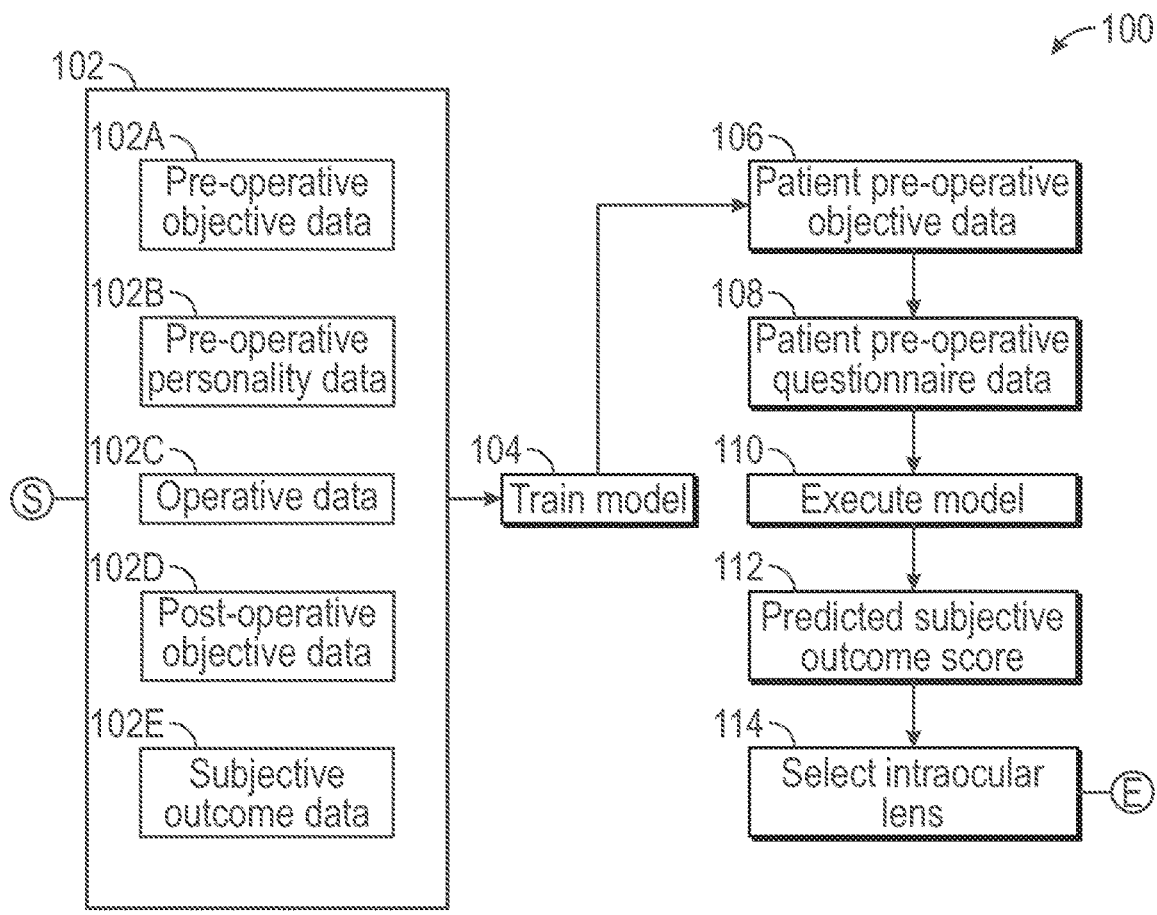
FIG. 2 is a schematic flowchart for a method executable by the controller of FIG. 1.

Referring now to FIG. 2, a flow chart of method 100 executable by the controller C of FIG. 1 is shown. Method 100 need not be applied in the specific order recited herein and some blocks may be omitted. The memory M can store controller-executable instruction sets, and the processor P can execute the controller-executable instruction sets stored in the memory M.

Per block 102 of FIG. 2, the controller C is configured to collect one or more training datasets, for example, from the remote server 40 via the long-range network 44. The training dataset includes respective historical sets composed of respective pre-operative objective data (block 102A), respective pre-operative personality data (block 102B), respective intra-operative data (block 102C), respective post-operative objective data (block 102D), and respective subjective outcome data (block 102E). In block 104, the controller C is configured to calibrate or train the machine learning model 40 with the training dataset from block 102.

For block 102A, the respective pre-operative objective data may include anatomic eye measurements (e.g., eye length, corneal topography and thickness, lens position and thickness, etc.), refractive eye measurements (e.g., classical refraction, wavefront aberrometry) and physiologic eye measurements (e.g., intraocular pressure, tear film health, etc.). The respective pre-operative objective data (block 102A) may include further visual function measurements (e.g., photopic/mesopic visual acuity, contrast sensitivity, near vision, etc.). Additionally, the controller C may be configured to identify and screen out the respective historical sets having at least one variable in the respective pre-operative objective data matching with a predefined confounding parameter. For example, if the confounding parameter is previous eye surgery, the corresponding data set may be left out of the training dataset.

For block 102B, the respective pre-operative personality data may include a visual needs assessment or lifestyle demands (dominant activities, e.g., needlepoint versus fishing) and a personality trait. A standardized assessment may be used to obtain consistent data across patients and sites. In one example, the Big Five Factor model of personality type, sometimes known as McCrae and Costa, may be employed. The Big Five Factor model posits that the traits of openness, conscientiousness, extraversion, agreeableness and neuroticism (or emotional stability) form the basis of people's personalities (see McCrae, R., Costa, P., *Personality in Adulthood: A Five-Factor Theory Perspective*, Guilford Press, New York City (2003). In one example, the personality trait may be represented as a numerical scale of agreeability, e.g., on a scale of 1 to 10, how agreeable is a person. In another example, the personality trait may be expressed as a binary result: either predominantly agreeable or predominantly non-agreeable.

For block 102C, the respective intra-operative data (block 102C) may include information related to the actual treatment performed. This information may be captured electronically and fed into the data management module 62. Examples of intra-operative data include, but are not limited to, the type of refractive surgery procedure performed, the model of the implanted intraocular lens and its prescription. The intra-operative data may include intra-operative aberrometry measurements. The intra-operative data may further include the surgical machine settings and parameters of the procedure, such as procedure time, the temperature of the operating room, the total phaco power consumed to emulsify the original lens, the time duration that the phaco energy was applied, and the effective phaco time (as a product of phaco time multiplied by an average phaco power). The intra-operative data may further include: the type of delivery device used to implant the intraocular lens, the presence or absence of any occlusion breaks, the quantity and degree of the occlusion breaks, and whether or not assistive devices (such as capsular hooks) were employed. The intra-operative data may further include an intra-operative grade of nuclear hardness of the original lens, which may be graded according to a lens opacity classification.

For block 102D, the respective post-operative objective data may include objective, measurable information obtained post-operatively for each patient in the training dataset. The respective post-operative objective data may include anatomic eye measurements (e.g., eye length, corneal topography and thickness, lens position and thickness, etc.), refractive eye measurements (e.g., classical refraction, wavefront aberrometry), physiologic eye measurements (e.g., intraocular pressure, tear film health, etc.) and visual function measurements (e.g., photopic/mesopic visual acuity, contrast sensitivity, near vision, etc.).

For block 102E, the respective subjective outcome data in the respective historical sets may include one or more numerical satisfaction scale that reflects satisfaction with the post-operative visual outcome. The patient's satisfaction with their surgical outcome may be captured at one or more specific time periods (e.g. at 1 month and at 3 months post-surgery). In one example, a single overall satisfaction is employed, based on the following question: "on a scale of 1-5 (with 5 being best), how happy are you with your vision now?" In another example, separate satisfaction scales may be employed for near vision, far vision, night/dim light vision, "outdoor sports vision" (e.g. playing golf) and overall satisfaction.

The controller C may be configured to quantify correlation of the respective post-operative objective data to the respective subjective outcome score in the respective historical sets and identify the respective post-operative objective data most strongly correlating with the respective subjective outcome score. In other words, the system 10 will look at the objective post-operative measurements and assess how much those influence the questionnaire responses (respective subjective outcome data). This provides two technical advantages. First, this enables identification of objective post-operative measurements that drive patient satisfaction/dissatisfaction, and second, this enables screening of patients with confounding outcome parameters. For example, he controller C may be configured to screen out the respective historical set if the respective post-operative objective data exceeds a threshold, e.g., if the post-operative refraction was more than a half diopter from intended.

Referring now to block 106 of FIG. 2, the controller C is configured to obtain pre-operative objective data for the patient P at the clinic 70. The pre-operative objective data may include anatomic eye measurements (e.g., eye length, corneal topography and thickness, lens position and thickness, etc.), refractive eye measurements (e.g., classical refraction, wavefront aberrometry), physiologic eye measurements (e.g., intraocular pressure, tear film health, etc.) and visual function measurements (e.g., photopic/mesopic visual acuity, contrast sensitivity, near vision, etc.).

Per block 108 of FIG. 2, the controller C is configured to obtain pre-operative questionnaire data for the patient, including at least one personality trait. As noted above, standardized methods may be used to assess the personality trait of the patient P. In one example, the personality trait of the patient P may be represented as a numerical scale of agreeability. In another example, the personality trait may be expressed as a binary result such that the patient P is either predominantly agreeable or predominantly non-agreeable. The pre-operative questionnaire data may further include a lifestyle needs assessment for the patient P.

Per block 110 of FIG. 2, the method 100 includes entering the pre-operative objective data and the pre-operative questionnaire data as respective inputs to the machine learning model 40 and executing the machine learning model 40. Per block 112 of FIG. 2, the controller C is configured to generate a predicted subjective outcome score for the patient P for the first intraocular lens 12 as an output of the machine learning model 40. Blocks 102 to 112 may be repeated to obtain a predicted subjective outcome score for the patient P for the second intraocular lens 22 and other types of intraocular lenses. Alternatively, the training datasets may encompass multiple types of intraocular lenses, with the type of intraocular lens incorporated as an element of block 102C.

Per block 114, the method 100 includes selecting the appropriate intraocular lens L based in part on a comparison of the predicted subjective outcome score for the first intraocular lens 12, second intraocular lens 22 and other lenses. For example, if the predicted subjective outcome score is 85% for the first intraocular lens 12, and 30% for the second intraocular lens 22, a bilateral implantation of the first intraocular lens 12 may be optimal. If the predicted subjective outcome score is 55% for the first intraocular lens 12, and 60% for the second intraocular lens 22, the refractive outcome may be optimized with a "blended" solution, i.e., implanting the second intraocular lens 22 in the dominant eye and the first intraocular lens 12 in the non-dominant eye.

The system 10 may be configured to be "adaptive" and may be updated periodically after the collection of additional data for the training datasets. In other words, the machine learning models 40 may be configured to be "adaptive machine learning" algorithms that are not static and that improve after additional training datasets are collected. The machine learning models 40 of FIG. 1 may be configured to find parameters, weights or a structure that minimizes a respective cost function and may incorporate respective regression models. The machine learning models 40 of FIG. 1 may include a neural network, an example of which is shown in FIG. 3.

Figure 3:
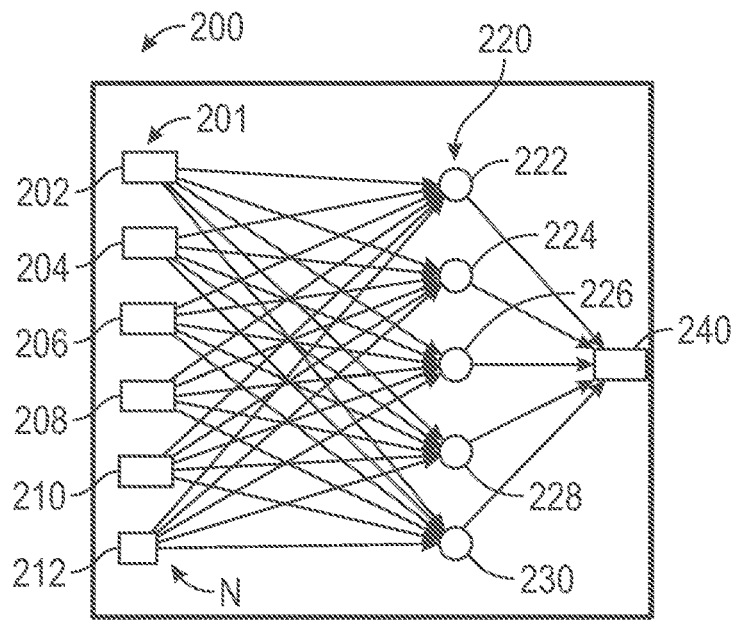
FIG. 3 is a schematic example of a neural network executable by the controller of FIG. 1.

Referring to FIG. 3, the neural network 200 is a feedforward artificial neural network having at least three layers, including an input layer 201, at least one hidden layer 220 and an output layer 240. Each layer is composed of respective nodes N configured to perform an affine transformation of a linear sum of inputs. The respective nodes N are characterized by a respective bias and respective weighted links. The parameters of each respective node N may be independent of others, i.e., characterized by a unique set of weights. The input layer 201 may include first input node 202, second input node 204, third input node 206, fourth input node 208, fifth input node 210 and sixth input node 212. The respective nodes N in the input layer 201 receive the input, normalize them and forward them to respective nodes N in the hidden layer 220.

Referring to FIG. 3, the hidden layer 220 may include first hidden node 222, second hidden node 224, third hidden node 226, fourth hidden node 228 and fifth hidden node 230. Each respective node N in a subsequent layer computes a linear combination of the outputs of the previous layer. A network with three layers would form an activation function $f(x)=f(3)(f(2)(f(1)(x)))$. The activation function $f$ may be linear for the respective nodes N in the output layer 240. The activation function $f$ may be a sigmoid for the hidden layer 220. A linear combination of sigmoids may be used to approximate a continuous function characterizing the output vector y. The patterns recognized by the neural network 200 may be translated or converted into numerical form and embedded in vectors or matrices.

The machine learning models 40 may employ deep learning maps to match an input vector x to an output vector y by learning an activation function $f$ such that $f(x)$ maps to y. A training process enables the machine learning models 40 to correlate the appropriate activation function $f(x)$ for transforming the input vector x to the output vectory. For example, in the case of a simple linear regression model, two parameters are learned: a bias and a slope. The bias is the level of the output vector y when the input vector x is 0 and the slope is the rate of predicted increase or decrease in the output vectory for each unit increase in the input vector x. Once the machine learning models 40 are trained, estimated values of the output vectory may be computed with new values of the input vector x.

In summary, the system 10 and method 100 optimize the selection process for an intraocular lens L, utilizing parameters from both an objective and subjective standpoint. The system 10 and method 100 provide objective guidance to both clinicians and patients, based on the patient's detailed pre-operative information as well as a database of prior cases, incorporating both subjective and objective information as well as details of the surgical procedure applied in each case.

The controller C of FIG. 1 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, punch cards, paper tape, other physical medium with patterns of holes, a RAM, a PROM, an EPROM, a FLASH-EEPROM, other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims.

Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A system for selecting an intraocular lens for implantation into an eye of a patient, the system comprising:
   a controller having a processor and a tangible, non-transitory memory on which instructions are recorded;
   wherein the controller is configured to selectively execute at least one machine learning model, the at least one machine learning model being trained with a training dataset which includes respective historical sets comprising each of respective pre-operative objective data, respective pre-operative personality data, respective intra-operative data, respective post-operative objective data, and respective subjective outcome data;
   wherein execution of the instructions by the processor causes the controller to:
   obtain pre-operative objective data for the patient, including one or more anatomic eye measurements;
   obtain pre-operative questionnaire data for the patient, including at least one personality trait;
   enter the pre-operative objective data and the pre-operative questionnaire data as respective inputs to the at least one machine learning model and generate a predicted subjective outcome score for the patient as an output of the at least one machine learning model; and
   select the intraocular lens based in part on the predicted subjective outcome score.

2. The system of claim 1, wherein:
the at least one machine learning model includes a neural network.

3. The system of claim 1, wherein:
the at least one personality trait of the patient is represented as at least one of a numerical scale of agreeability or as a binary result, the binary result being either predominantly agreeable or predominantly non-agreeable.

4. The system of claim 1, wherein:
the pre-operative questionnaire data further includes a lifestyle needs assessment for the patient.

5. The system of claim 1, further comprising:
an integrated diagnostic device configured to obtain the pre-operative objective data; and
wherein the pre-operative objective data further includes refractive eye measurements and physiologic eye measurements.

6. The system of claim 1, further comprising:
a data management module accessible to the controller, the data management module being configured to collect the respective historical sets from a plurality of electronic medical record units.

7. The system of claim 1, wherein:
the respective subjective outcome data in the respective historical sets includes a numerical satisfaction scale.

8. The system of claim 1, wherein the controller is configured to:
quantify a correlation of the respective post-operative objective data to the respective subjective outcome score in the respective historical sets; and
identify the respective post-operative objective data most strongly correlating with the respective subjective outcome score.

9. The system of claim 1, wherein the controller is configured to:
identify and screen out the respective historical sets having at least one variable in the respective pre-operative objective data matching with a predefined confounding parameter.

10. A method of selecting an intraocular lens for implantation in an eye, the method comprising:
receiving, via a controller, pre-operative objective data for a patient, including one or more anatomic eye measurements;
receiving, via the controller, pre-operative questionnaire data for the patient, including at least one personality trait;
executing an at least one machine learning model with the preoperative objective data and the pre-operative questionnaire data as respective inputs, via the controller, the at least one machine learning model being trained with a training dataset which includes each of respective historical sets composed of respective pre-operative objective data, respective pre-operative personality data, respective intra-operative data, respective post-operative objective data, and respective subjective outcome data;
generating, as an output of the at least one machine learning model, a predicted subjective outcome score for the patient; and
selecting the intraocular lens based in part on the predicted subjective outcome score.

11. The method of claim 10, wherein:
representing the at least one personality trait of the patient as at least one of a numerical scale of agreeability or as a binary result, the binary result being either predominantly agreeable or predominantly non-agreeable.

12. The method of claim 10, wherein:
the pre-operative questionnaire data further includes a lifestyle needs assessment for the patient.

13. The method of claim 10, further comprising:
obtaining, from an integrated diagnostic device, the pre-operative objective data; and
wherein the pre-operative objective data further includes refractive eye measurements and physiologic eye measurements.

14. The method of claim 10, further comprising:
collecting, via a data management module, the respective historical sets from a plurality of electronic medical record units; and
delivering the respective historical sets to the at least one machine learning module.

15. The method of claim 10, wherein:
the respective subjective outcome data in the respective historical sets includes a numerical satisfaction scale.

16. The method of claim 10, further comprising:
assessing a respective correlation of the respective post-operative objective data to the respective subjective outcome score in the respective historical sets, via the controller; and
identifying the respective post-operative objective data most strongly correlating with the respective subjective outcome score, via the controller.

* * * * *